(12) United States Patent
Merchant

(10) Patent No.: US 6,709,460 B2
(45) Date of Patent: Mar. 23, 2004

(54) PATELLAR BEARING IMPLANT

(76) Inventor: Alan C. Merchant, 124 Marvin Ave., Los Altos, CA (US) 94022

(*) Notice: Subject to any disclaimer, the term of this patent is extended or adjusted under 35 U.S.C. 154(b) by 0 days.

(21) Appl. No.: 09/810,803

(22) Filed: Mar. 15, 2001

(65) Prior Publication Data

US 2001/0037155 A1 Nov. 1, 2001

Related U.S. Application Data

(60) Provisional application No. 60/190,793, filed on Mar. 21, 2000, and provisional application No. 60/191,954, filed on Mar. 24, 2000.

(51) Int. Cl.[7] .................................................. A61F 2/38
(52) U.S. Cl. ..................................... 623/20.2; 623/20.18
(58) Field of Search ........................... 623/20.18, 20.19, 623/20.2

(56) References Cited

U.S. PATENT DOCUMENTS

| 4,151,615 A | 5/1979 | Hall |
| 4,158,894 A | 6/1979 | Worrell |
| 4,240,162 A | 12/1980 | Devas |
| 4,309,778 A | 1/1982 | Buechel et al. |
| 4,340,978 A | 7/1982 | Buechel et al. |
| 4,470,158 A | 9/1984 | Pappas et al. |
| 4,964,867 A | 10/1990 | Boger |
| 5,011,496 A | 4/1991 | Forte et al. |
| 5,383,937 A | 1/1995 | Mikhail |
| 5,480,443 A | 1/1996 | Elias |
| 5,609,640 A | 3/1997 | Johnson |
| 5,702,467 A | 12/1997 | Gabriel et al. |
| 5,824,098 A | 10/1998 | Stein |

FOREIGN PATENT DOCUMENTS

| DE | 4310968 A1 | 10/1994 |
| EP | 0582514 A1 | 8/1993 |
| EP | 0307654 B1 | 1/1994 |
| EP | 0685210 B1 | 5/1995 |
| FR | 2594323 A1 | 2/1986 |
| FR | 2700260 A1 | 1/1993 |

*Primary Examiner*—David J. Isabella
*Assistant Examiner*—Urmi Chattopadhyay
(74) *Attorney, Agent, or Firm*—Townsend and Townsend and Crew LLP

(57) ABSTRACT

A patellar bearing having extended, rounded contours on the superior and inferior edges of its articulating surface.

2 Claims, 3 Drawing Sheets

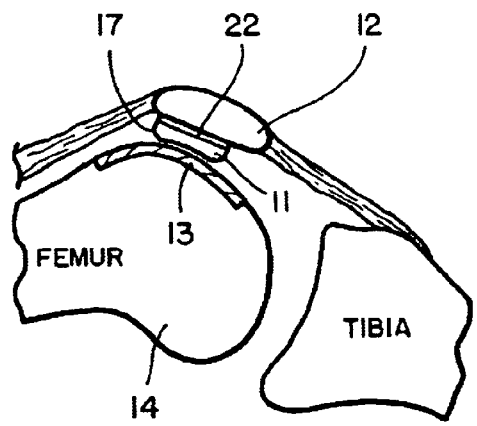
FIG_1A
(PRIOR ART)
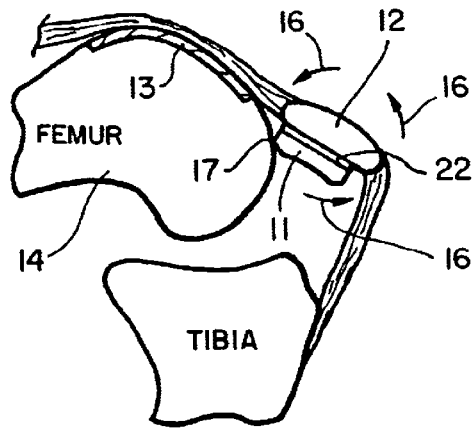
FIG_1B
(PRIOR ART)
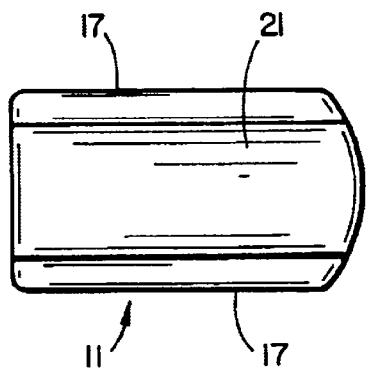
FIG_2A
(PRIOR ART)
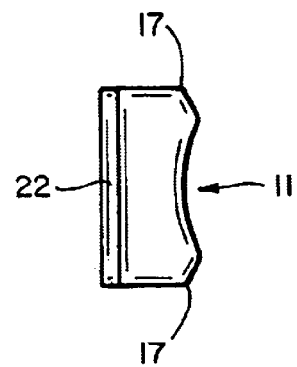
FIG_2B
(PRIOR ART)

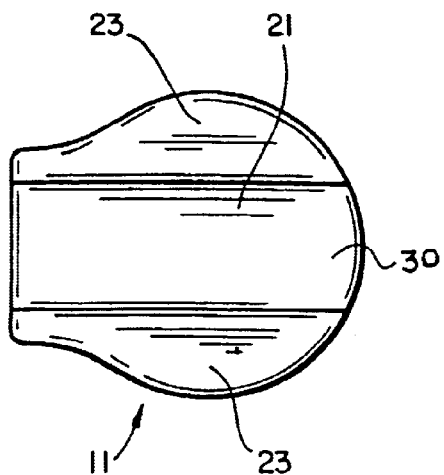
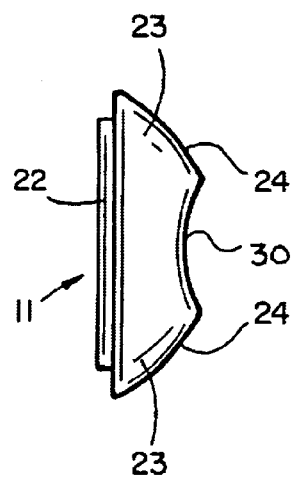
FIG_3A  FIG_3B
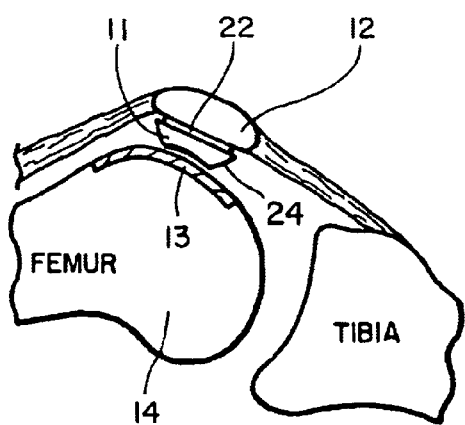
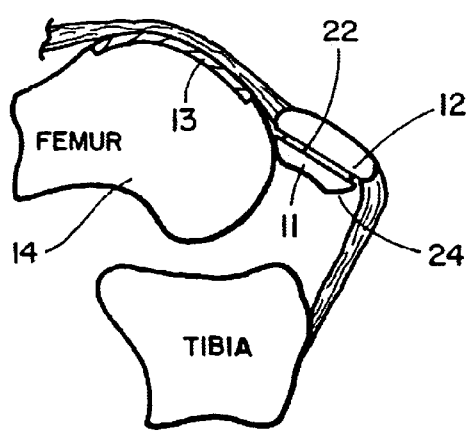
FIG_5A  FIG_5B

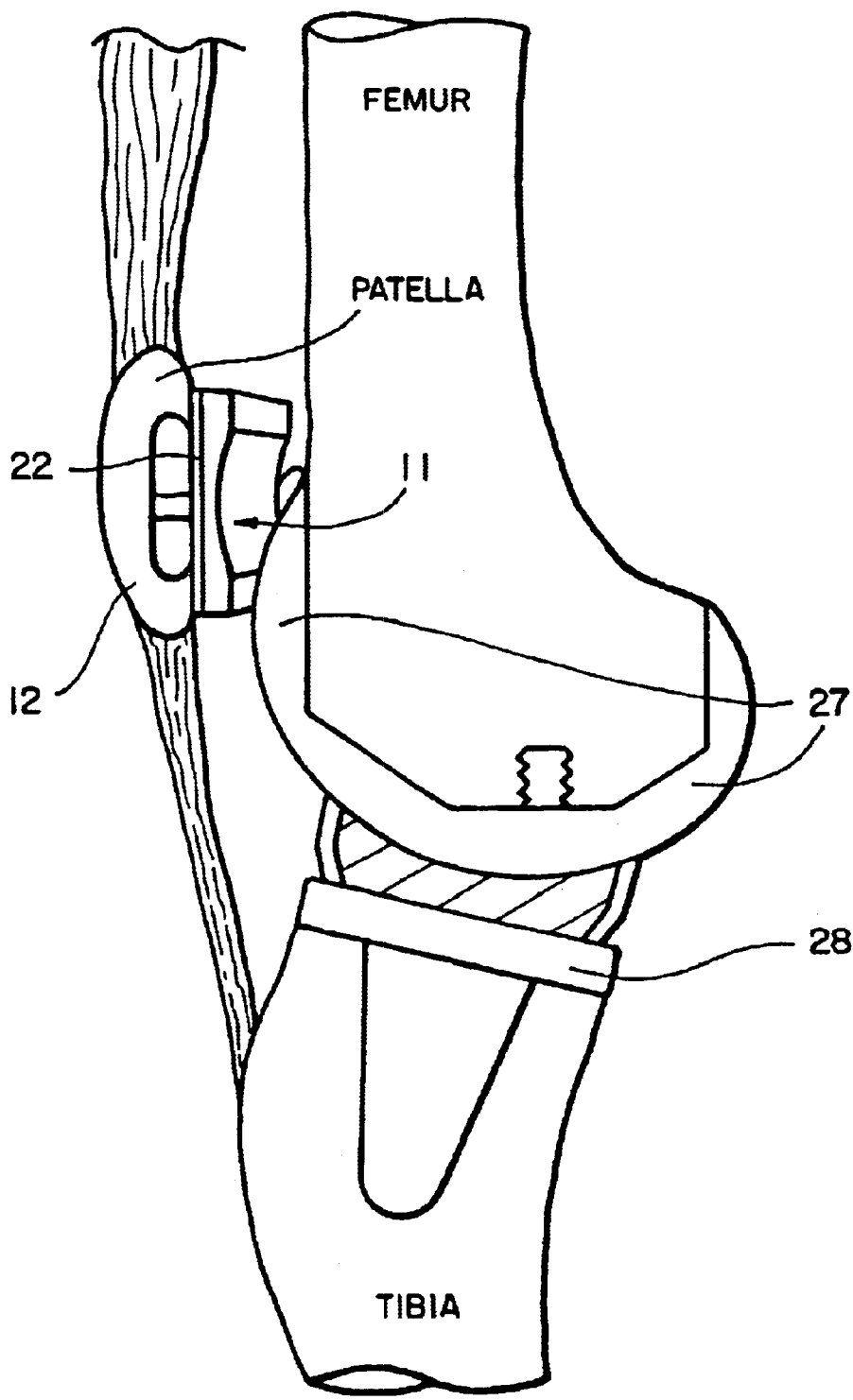
FIG_4
*(PRIOR ART)*

PATELLAR BEARING IMPLANT

RELATED APPLICATIONS

This application claims priority to U.S. Provisional Application Serial No. 60/190,793 filed Mar. 21, 2000 and U.S. Provisional Application Serial No. 60/191,954 filed Mar. 24, 2000.

BRIEF DESCRIPTION OF THE INVENTION

The invention relates to an improved patellar bearing for a prosthetic knee joint that will reduce or eliminate the sudden posterior rotation "clunk" of the patella (knee cap) with its implant, especially in knees with low patellar position in relation to the joint line.

BACKGROUND OF THE INVENTION

When, due to disease or injury, the articulating surfaces of a knee joint become sufficiently disabling and painful (arthritic), these surfaces are commonly replaced using a surgical operation, either in whole or in part, by prosthetic implants. The most commonly performed operation of this kind is the replacement of all of the joint surfaces in the knee, referred to as a total knee replacement. Sometimes the damage is limited to only one side of the knee joint, either the medial (the side toward the midline of the body) or the lateral (the side away from the midline of the body) compartment. Then, the operation to replace just these damaged surfaces between the femur (thigh bone) and the tibia (leg bone) is referred to as a unicompartmental replacement. A unicompartmental replacement can be either medial or lateral. Sometimes the damage is limited to the joint surfaces between patella (knee cap) and the femoral groove with which the patella articulates. In this case, the operation to replace these joint surfaces is called a patellofemoral replacement.

A multitude of different designs of total or partial knee replacement systems have evolved over time using various metals, plastics, and ceramics as the bearing surfaces. Naturally, all these bearing surfaces are subject to wear giving rise to failure of the bearing, fracture of the bearing, or loosening of the implant over time. When this happens, another operation is required to replace or revise the implant(s). This is referred to as a revision replacement. Because this is a second operation performed on already altered bone, tendons, ligaments, and muscles comprising the joint, the results are not as good compared to the initial or primary joint replacement operation. Therefore, an important common goal of all joint replacement systems is to provide a comfortable, functioning joint that lasts for the life of the patient.

The total knee replacement prosthesis design that apparently has the best-reported longevity along with the lowest reported complication rate involving the patella is the design by Buechel and Pappas, U.S. Pat. Nos. 4,309,778 (1982), 4,340,978 (1982), and 4,470,158 (1984). Among the design features of this patellar prosthesis that have contributed to its superior longevity and low complication rate are: (1) the deeper (compared to other patellar prosthetic designs), V-shaped contours of the posterior articulating bearing that resists displacement or dislocation from the femoral groove with which it articulates; (2) the broad, congruent bearing surfaces providing area contact loading (as opposed to dual point contact or line contact loading as in other patellar prosthetic designs) that reduces contact stress and thus reduces wear; and (3) the provision for the plastic patellar bearing to rotate on a cone-shaped trunion of the metal base plate causing this rotating patellar bearing to act in a self-aligning manner and thus further reduce stress, wear, and loosening. This patellar prosthesis is known as the low contact stress, or LCS, rotating patella.

FIGS. 1A and 1B show a total patellofemoral implant employing a prior art LCS patellar bearing 11 implanted into the patella 12. A trochlear component 13 is shown implanted in the femur 14. FIG. 1A shows the knee flexed at about 45°. FIG. 1B shows the knee flexed to about 120°. It is seen that the patella, with its implanted prosthesis, suddenly rocks, arrows 16, over the sharp and angular superior edge 17 of the LCS patellar bearing.

This feature of the prior art LCS rotating patellar bearing is deleterious, detrimental and disadvantageous. When this patellar prosthesis is implanted into a patient either for a total knee replacement or for a modular total patellofemoral replacement (see my U.S. patent application Ser. No. 09/148,110 filed Sep. 4, 1998) and the patient has a low riding patella, as referenced from the joint line between the femur and the tibia, an annoying and painful symptom described by patients as a "clunk" will likely occur. Patients with patellas positioned lower than average are said to have "patella infera", a congenital or acquired condition. The opposite condition is referred to as "patella alta". The aforementioned annoying and painful "clunk" starts occurring when the patients with patella infera have regained their normal range of motion after surgery. As the patient flexes (bends) the knee beyond a right angle, the patella that is already low to begin with slides farther around the curvature at the lower end of the femur and reaches a point where it suddenly rocks back over the sharp and angular superior edge of the plastic patellar bearing. This sudden posterior rotation of the patella and its implanted bearing occurs around a transverse axis of the patella and is felt by the patient as a sudden, annoying, and painful "clunk".

The sharp, angular superior edge of the aforementioned patellar prosthesis bearing also has the potential to damage the normal articular cartilage in the knee when the prosthesis is implanted for a total patellofemoral replacement. When a total patellofemoral replacement operation is performed, the entire patellar articular surface is replaced, but only the anterior groove on the front of the femur (the trochlea) is replaced, not the entire articular surface on the lower end of the femur. The remaining normal cartilage on the end of the femur is purposely left intact to articulate with the remaining normal cartilage on the upper end of the tibia. After a total patellofemoral replacement, when the patient flexes (bends) the knee beyond a right angle, the patellar prosthesis moves farther around the curve of the lower end of the femur progressively leaving its contact with the metal trochlear implant and making greater and greater contact with the remaining normal cartilage. The sharp and angular superior corner of the LCS prosthetic patellar bearing can press into, gouge, or damage the softer normal articular cartilage.

An improvement in the aforementioned patellar bearing to eliminate or reduce the sudden, annoying, and painful symptom experienced by patients as a "clunk" is beneficial and desirable. Said improvement would also lessen the risk of damage to the normal articular cartilage when the patellar bearing is used for a total patellofemoral replacement.

THE OBJECTS AND SUMMARY OF THE INVENTION

The objects and advantages of the present invention are:

(a) to reduce or eliminate the sudden posterior rotation "clunk" experienced by certain patients who have had the Low Contact Stress (LCS) patellar prosthesis implanted during total knee replacement or total patellofemoral replacement, and (b) to reduce or eliminate articular cartilage damage caused by the sharp and angular superior edge of the aforementioned patellar prosthesis when it has been implanted during a total patellofemoral replacement.

The improved patellar bearing has an extended superior-to-inferior dimension with rounded contours on the superior and inferior edges of its joint surface that articulates with either a femoral prosthetic component or a trochlear prosthetic component.

DESCRIPTION OF DRAWINGS

The foregoing and other objects of the present invention will be more clearly understood from the following description when read in conjunction with the accompanying drawings in which:

FIGS. 1A and 1B are side views of a knee with a patellofemoral replacement employing a prior art patellar bearing with different degrees of flexion.

FIGS. 2A and 2B show front and end views of a prior art patellar bearing.

FIGS. 3A and 3B show front and end views of a patellar bearing in accordance with the present invention.

FIG. 4 shows a prior art LCS patellar bearing in a total knee replacement.

FIGS. 5A and 5B are side views of a knee with a patellofemoral implant employing a patellar bearing in accordance with the present invention with different degrees of flexion.

DESCRIPTION OF INVENTION—PREFERRED EMBODIMENT

A prior art LCS patellar bearing is shown in FIGS. 2A and 2B. FIG. 2A is a posterior or articular surface view and FIG. 1B is a side view. The patellar implant 11 includes a plastic bearing 21 attached to a metallic plate 22. Note particularly the sharp, angular edges 17. The preferred embodiment of the present invention is illustrated in FIGS. 3A (posterior, or articular surface, view) and 3B (side view). The plastic bearing 21 is shown on its metallic base plate 22. In the preferred embodiment the base plate is made of chrome-cobalt-molybdenum alloy and the bearing is made from high-density polyethylene (HDPE). The superior and inferior dimensions of the bearing have been increased 23. The sharpened angular superior and inferior edges 17 on the articular bearing surface that engages the femoral component in a total knee replacement or a trochlear component in a total patellofemoral replacement have been eliminated. Instead, the superior-to-inferior dimension has been increased and the superior and inferior articular bearing surfaces are made to have a smooth and rounded contour 24, where the rounded contours are aligned along linear junctions on both sides of an axial concave surface 30 which engages the femoral or trochlear component of the implant. The smooth rounded contours extend from the junctions to a bottom of the articular bearing surface without regions of flatness. Because all the prosthetic components are made in various sizes in order to match various sizes o patients from small to extra large, the added superior and inferior dimensions and the radii of curvature for the rounded contours vary proportionately according to the sizes.

Alternate embodiments are possible, now or in the future, using alternate materials such as ceramics, different metal alloys, and different plastics. The main feature of prostheses and their articular bearing surfaces is well-known and the manufacture of the patellar implant is not described.

The present invention replaces the older LCS bearing when a patellar prosthesis is used in either a total knee replacement operation or a total patellofemoral replacement operation. FIG. 4 shows a prior art LCS patellar bearing 11 and base plate 22 implanted into a patella 12. The femoral component 27 and the tibial component 28 are shown implanted into the femur and tibia respectively to complete a total knee replacement. FIGS. 1A and 1B, previously described, show the old LCS bearing 11 and base plate 22 implanted into a patella 12, and a trochlear component 13 implanted in the femur to complete a total patellofemoral replacement.

FIG. 1A shows a side view of the prior art patellar bearing 11 and the base plate 22 implanted into a patella 12 wherein the knee is flexed at 45°. FIG. 1B shows what can happen when the knee is flexed farther to about 120°. The patella with its implanted prosthesis suddenly rocks back over the sharp and angular edge of the old LCS bearing with an annoying and painful "clunk". The arrows 16 in FIG. 1B depict the direction of sudden rotation of the patellar implant that occurs around an imaginary transverse axis through the patella.

FIG. 5A shows a side view of my novel LCS patellar implant 11 and its base plate 22 implanted into a patella 12 wherein the knee is flexed 45°. FIG. 5B shows what happens when the knee is flexed farther to about 120°. The smooth and rounded contour 24 of the superior edge of the improved bearing allows the patella to rotate smoothly and gradually eliminating or reducing the sudden annoying and painful "clunk".

Because the patellar prosthesis can be used in either a right or a left knee by reversing it, both the superior and inferior margins are extended and contoured.

It can be seen that this improved bearing of the present invention can be exchanged for the old LCS rotating plastic bearing to eliminate or reduce the annoying and painful sudden patellar "clunk" in both total knee replacements and total patellofemoral replacements in patients who have a tendency to have patella infera.

The present invention will also reduce and minimize damage to the normal articular cartilage remaining in a knee after total patellofemoral replacement by eliminating the sharp and angular edge of the old LCS patellar bearing and replacing it with the present invention that has a smooth and rounded contour.

What is claimed is:

1. A patellar implant comprising:
   a base plate and an articular bearing surface rotatably mounted on the base plate for engaging the femoral component in a total knee replacement or a trochlear component in a total patellofemoral replacement, characterized in that:
   said bearing surface of the patellar implant has a superior articular surface and an inferior articular surface, wherein said surfaces have smooth rounded contours (24) aligned along linear junctions on both sides of an axial concave surface (30) which is adapted to engage the femoral or trochlear component, wherein said smooth rounded contours extend from the junctions to a bottom of the articular bearing surface without regions of flatness.

2. A patellar implant as in claim 1 in which the base plate is made of chrome-cobalt-molybdenum alloy and the bearing surface is high-density polyethylene.

* * * * *